Figure 1:
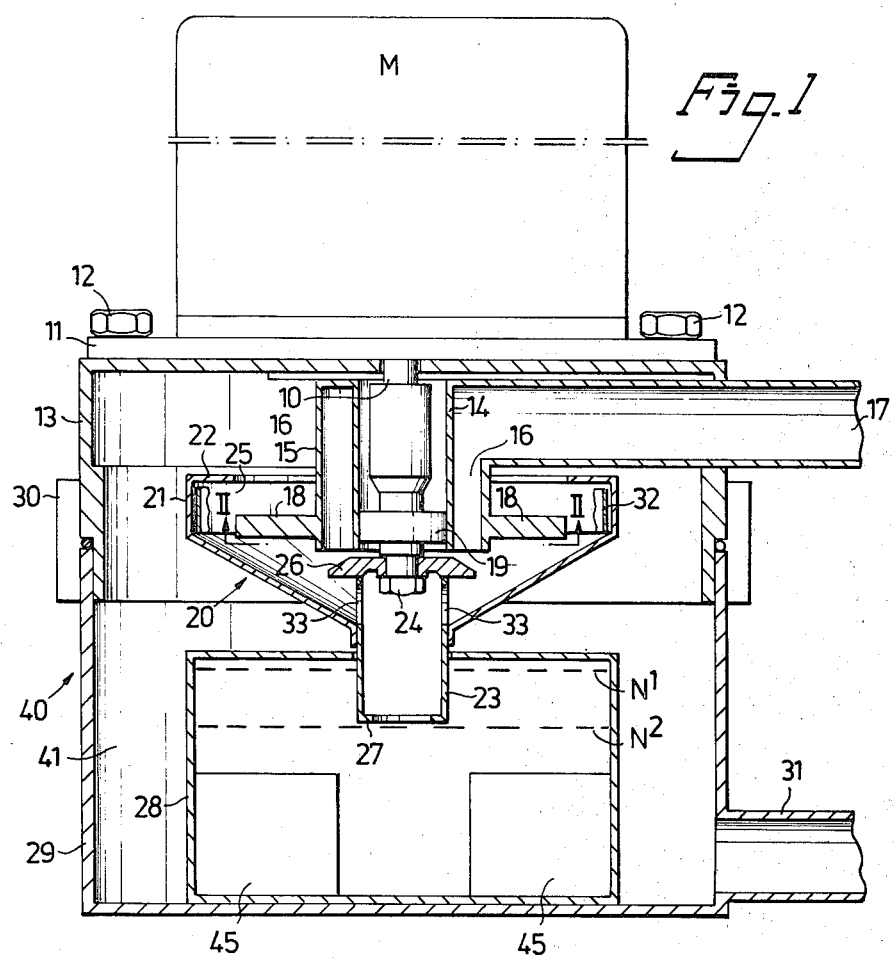

United States Patent [19]

Rosander

[11] 4,356,959
[45] Nov. 2, 1982

[54] METHOD PARTICULARLY INTENDED FOR SEPARATING MERCURY COMPOUNDS AND MERCURY ALLOYS IN SOLID PARTICLE FORM FROM A FLUID, AND AN APPARATUS FOR CARRYING OUT THE METHOD

[75] Inventor: Jan Rosander, Gothenburg, Sweden
[73] Assignee: Scania Dental AB, Knivsta, Sweden
[21] Appl. No.: 176,463
[22] Filed: Aug. 8, 1980
[30] Foreign Application Priority Data
Aug. 17, 1979 [SE] Sweden .............................. 7906892
[51] Int. Cl.$^3$ ............................ B04B 1/00; B04B 7/04
[52] U.S. Cl. .................................... 233/27; 233/1 A; 233/21
[58] Field of Search ...................... 233/1 A, 27, 28, 33, 233/34, 44, 45, 21, 22, 16, 19 R, 19 A, 2

[56] References Cited
U.S. PATENT DOCUMENTS 2,083,809  6/1937  Asch ....................................... 233/45
2,905,380  9/1959  Matthews .............................. 233/27
3,861,584  1/1975  Dudrey .................................. 233/27
3,863,838  2/1975  Pronk .................................... 233/27

Primary Examiner—Robert W. Jenkins
Attorney, Agent, or Firm—Hammond & Littell, Weissenberger & Muserlian

[57] ABSTRACT

An apparatus for separating solid particles, particularly mercury compounds and alloys, from a fluid, such as dental waste water, contaminated therewith, comprising a rotatable container to receive contaminated fluid, said container having a vertical peripheral wall and an upper horizontal wall depending from the outer periphery thereof to collect particles centrifugally urged thereagainst owing to the rotation of said container, and means at the lower part of said rotatable container communicating with a collecting means for recovering a mixture of fluid and particles having been collected at the peripheral part of said container. When the container ceases to rotate, the particles held at the periphery of the vessel are caused to pass gravitationally into a vessel communicating with the container.

9 Claims, 2 Drawing Figures

METHOD PARTICULARLY INTENDED FOR SEPARATING MERCURY COMPOUNDS AND MERCURY ALLOYS IN SOLID PARTICLE FORM FROM A FLUID, AND AN APPARATUS FOR CARRYING OUT THE METHOD

The present invention relates to a method particularly, although not exclusively, intended for separating mercury compounds and mercury alloys in solid particle form from a fluid containing said compounds or alloys.

The invention also relates to an apparatus for carrying out the method.

In principle, it is desirable to separate from process water all solid particles which may be present therein, since these particles often contain substances which are harmful to the environment and which should be prevented from being dispersed via conventional sewage systems.

The field for which the present invention is particularly, although not exclusively, intended is the dental field. Within this field, substances, such as amalgam, containing mercury are handled daily. As will be appreciated, relatively large quantities of water contaminated with mercury are discharged through the sewage network via the suction systems used in dental practices, i.e. suction apparatus used for different purposes, such as mouth rinsing etc.

Apparatus for treating such contaminated fluids have previously been proposed, e.g. filter arrangements which filter out solid particles of a given size. These filters, however, become blocked relatively quickly by collections of blood and saliva and, furthermore, insufficient attention has been paid to the small or very minute and light mercury-containing solid particles able to pass through the filter.

A further separation technique is described in Swiss Patent Specification No. 592.582, in which mercury-contaminated sewage water is brought into contact with surfaces of tin and/or zinc.

The present invention is based on the principle of a singular combination of separation by means of centrifugal force and sedimentation, and the object of the invention is to provide a method by which solid particles present in a fluid can be separated therefrom and which enables water continuously discharged to the sewage network to be highly purified.

Another object of the invention is to provide means for handling recoverable material in a hygienic fashion.

The method according to the invention is characterized in that an inlet line for contaminated sewage water discharges into a preferably annular space in which there is fixedly arranged in the lower part thereof a guide flange, in that said annular space is caused to communicate with the interior of a rotary part having an upper horizontal defining wall and being connected to the drive shaft of a motor; in that the flange and the defining wall of the rotary part are so arranged relative to one another that contaminated water is caused to flow into the rotatable part beneath said flange; that contaminated water is caused to rotate, whereat contaminant particles present in the sewage water are urged centrifugally substantially towards the peripheral wall of the rotating part; in that water freed from particles is caused to flow out between the space defined by the guide flange and the horizontal defining wall; and in that the rotary part exhibits a lower opening which, when the motor is stopped, acts as an outlet for the particles stored on said peripheral part.

For the purpose of carrying out the method according to the invention there is proposed an apparatus which is characterized in that a motor having a drive shaft is connected with a container having an upper part which exhibits an inlet for contaminated waste water and the lower part of which is provided with an outlet for purified waste water, whereat the contaminated waste water is arranged to flow down into a rotatable vessel which is rotated by said motor and which is provided with an upper horizontal defining wall; and in that there is provided a fixedly arranged horizontal flange oriented in a plane in which it is completely enclosed by the rotary vessel, whereat the contaminated waste water is arranged to flow out into the rotary vessel beneath the fixed flange and to be urged by the rotary movement of said vessel out towards the periphery thereof where the solid particles are stored, while the water freed from said particles flows out between the space defined by the horizontal defining wall of the rotary vessel and the guide flange; and in that the lower part of the rotary vessel is arranged to communicate with means for recovering the mixture of water and the particles stored at the periphery of the vessel, said particles falling down gravitationally when the vessel ceases to rotate.

Figure 2:
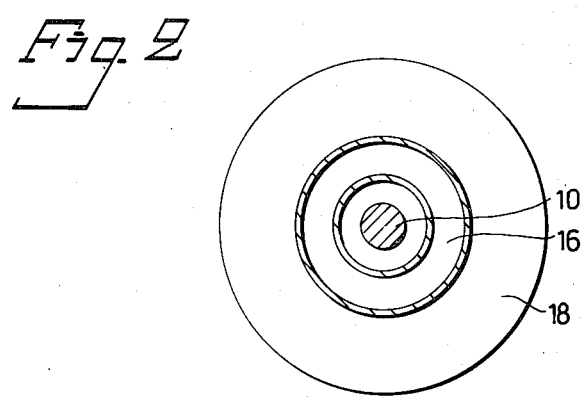

An exemplary embodiment of the invention will now be described in more detail with reference to the accompanying drawings, in which FIG. 1 is a vertical sectional view of an apparatus according to the invention, and FIG. 2 is a horizontal sectional view taken on the line II—II in FIG. 1.

A power source, which in the illustrated embodiment is an electric motor M of conventional design, is provided with an outwardly projecting drive shaft 10 and is connectable to the mains supply by means of a cable not shown. The motoris preferably a highspeed motor, having a speed of from 2000–5000 r.p.m. The motor M has a bottom plate 11 in which openings are provided through which screws 12 can be inserted for removably connecting the motor M to the upper part 13 of an annular or ring-shaped vessel generally identified at 40. The upper vessel part 13, which has a U-shaped cross section, has a central opening through which the drive shaft 10 of the motor M is inserted and which co-acts with a vertical sleeve which is concentrical with the drive shaft 10 and presents a clearance therewith. The sleeve 14 is so dimensioned that the drive shaft 10 projects outwardly of the lower opening of said sleeve. Arranged around the sleeve 14, concentrically therewith is a further sleeve 15, and the annular space formed between the sleeves 14 and 15 communicates with an inlet line 17 for contaminated fluid, originating from dental surgery. The outer sleeve 15 is provided at its lower end or in the vicinity of said end with a ring-shaped flange having a given radial extension. A packing box for the drive shaft 10 is shown at 19.

A container 20, which is preferably funnel-shaped, has a substantially vertically extending peripheral portion 21 which merges with a defining wall 22 extending horizontally towards the centre of the container 20. In this way there is formed in the upper part of the container 20 an opening of given size. The bottom part of the container 20 is provided with a sleeve-like shaft 23, the upper part of which is removably connected to the drive shaft 10 of the motor M. As will be understood, this connection results in rotation of the container 20 when the motor M is energized and can be of any conventional kind. In the illustrated embodiment the end of the drive shaft 10 remote from the motor M is provided with a bore having internal screw threads for receiving a screw 24 or equivalent screw-joint means. Although not shown in the drawing, the drive shaft 10 and the sleeve-like shaft 23 are provided with known spline joints.

In the exemplary embodiment of the invention, the rotatable container 20 is connected in the aforedescribed manner with the drive shaft 10 of the motor M and, as will be seen from the drawing, said container surrounds the radial flange 18 of the sleeve 15, preferably in a manner such that the end of the defining wall 22 extending towards the centre of the container 20 lies in substantially the same vertical plane as the end of the radial flange 18, and in a manner such as to form a ring-shaped gap 25 between said surface of radial flange 18 and the outer extension of defining 22. It will be evident from the mode of operation of the apparatus given hereinafter that this radial flange also serves as guide means for the fluid from which solid particles are to be removed.

As will also be seen from the drawing (FIG. 1), the upper end of the sleeve 23 has a radial flange 26 which forms a constriction in the mouth of the annular space 16. The lower end of the sleeve 23 has a 27 which extends radially inwardly and which forms a constriction.

The lower part of the sleeve 23 is arranged to extend into a further vessel 28 carried on the lower part 29 of the vessel 40 formed by the elements 13 and 29. The vessel element 29 is connected to the vessel element 13 by means of a quick-release coupling 30, thereby enabling the two elements to be readily disconnected from one another. The vessel element 29 is connected to a waste discharge system by means of a line 31.

The further vessel 28 is suitably of the disposable kind and is smaller than the vessel element 29, so as to form an annular space 41 which is arranged to communicate with the rotatable container 20 in a manner hereinafter described.

In accordance with one embodiment, the rotatable container 20 is provided with a slip ring or scraper ring 32 operative to scrape from said peripheral part any particles which may have adhered thereto.

The further vessel 28 may also be provided with lamella or other devices 45 for preventing rotation of fluid present in the vessel.

The function of the method and apparatus according to the present invention is as follows:

Saliva, cooling liquid and solid particles are carried away from the patient's mouth through a hose (not shown) into the inlet pipe 17 and are guided through the annular space 16, and enter the rotating container 20 at a location beneath the flange 18. As the container 20 rotates, the impurified liquid is urged centrifugally to the peripheral portion of the container 20.

During continued rotation of the container 20, the solid particles are stored substantially at or adjacent the peripheral portions of said container, while the fluid purified of said particles finds its ways through gap 25 and through the outlet 31, via the space 41, as liquid continuously flows through the inlet 17. This continuous outflow of purified fluid continues for as long as impure liquid flows through the inlet 17. It will be understood that when current to the motor M is broken, the container 20 will cease to rotate and the collection of fluid and solid particles present therein will fall gravitationally and flow through openings 33 in the sleeve 23, to settle on the bottom of the vessel 28. The vessel element 29 can then be disconnected from the vessel element 13 by means of the quick release coupling 30 and the vessel 28 removed and the contents thereof recovered. As will readily be understood, the vessel 28 may be replaced with any conventional form of collecting means.

The fluid passing through the outlet has a degree of purity lying immediately in the proximity of 100%. It will also be understood that the volume of fluid collected in the vessel 28, together with said particles, is very small, and hence said vessel, and therewith the apparatus as a whole, can be given small dimensions. When the apparatus is re-started, for example with a liquid level $N^1$ in the vessel 28, the volume of liquid present within the sleeve 23 will be thrown gravitationally towards the walls of the sleeve and out into the rotating container through the openings 33 in said sleeve 23, to be finally passed towards the peripheral part of the rotating container, and with impurified fluid again flowing through the inlet 17 the function of the apparatus is the same as that described above. The whole of the rotating unit forms a suction pump/fan which attempts to draw up a certain volume of liquid from the vessel 28 and thus releave the same of superfluous fluid. This suction effect on the fluid in the vessel 28 continues until the level $N^2$ has been reached. As before mentioned, when the container 20 ceases to rotate, a mixture of fluid and solid particles flows back to the vessel 28, forming a sediment on the bottom thereof.

The result of the aforedescribed effect is that approximately the same volume of fluid as that which is removed by suction from the vessel 28 when the motor is started and the container 20 rotates will return together with newly separated particles to the vessel 28 when the container ceases to rotate. In this way, the vessel 28 can never be overfilled. A further advantage is that waste amalgam is constantly collected in liquid in the vessel 28.

The removal of the vessel 28, and the optionary recovery of the solid particles present therein, need only take place over relatively long time intervals. Because the vessel 28 is of the disposable kind, which can readily be sealed and handled, the operator need never come into contact with the contents of said vessel, thereby ensuring that requirements with respect to hygiene are observed.

The aforementioned lamella or blades 45 arranged in the vessel 28 serve to prevent the sediment in the vessel from being stirred or agitated while the apparatus is in operation.

The invention is not restricted to the illustrated embodiment, but that said embodiment can be modified within the scope of the following claims. For example, the annular space 16 is not limited to the form exemplified in the drawing. The flow of contaminated liquid to the apparatus may also be effected in other ways, although the fluid shall be caused to flow into the rotating container at a location beneath the ring-shaped guide flange 18.

I claim:

1. An apparatus for separating solid particles, particularly mercury compounds and alloys, from a fluid, such as dental waste water, contaminated therewith, comprising a first vessel, a fluid inlet opening into a first annular space at the upper part of said vessel, an outlet for purified fluid at the lower part of said vessel, a rotatable container in communication with said first annular space to receive contaminated fluid therefrom, a motor having a drive shaft connected to said container centrally thereof for rotating the same, said container having a vertical peripheral wall and an upper horizontal wall depending from the outer periphery thereof to collect particles centrifugally urged thereagainst owing to the rotation of said container, a circular horizontal guide flange fixedly mounted at the bottom of said first annular space and surrounding the latter, said first annular space opening into said container beneath said flange to lead contaminated fluid into said container, said flange leaving a second annular space between the outer periphery thereof and the inner surface of said vertical peripheral wall for allowing the passage of contaminated fluid, a third annular space being defined between said upper horizontal wall and an outer wall surrounding said first annular space to conduct fluid liberated from said collected particles to a fourth annular space communicating with said outlet for purified fluid, and means at the lower part of said rotatable container communicating with a collecting means for recovering a mixture of fluid and particles having been collected at the peripheral part of said container on the cessation of rotation of said rotatable container.

2. An apparatus according to claim 1, wherein said means at the lower part of said rotatable container comprise an opening communicating with said collecting means.

3. An apparatus according to claim 2, wherein said collecting means is a disposable settling vessel.

4. An apparatus according to claim 1, wherein said first vessel comprises an upper vessel element removably connected to the motor, and a lower vessel element removably connected to said upper vessel element, said lower vessel element enclosing said collecting means.

5. An apparatus according to claim 4, wherein said upper vessel element is provided with a downwardly extending cylindrical tube enclosing said drive shaft with a clearance there between, and wherein outside said tube and concentrically therewith a sleeve is arranged into which said inlet discharges and which together with said tube defines said first annular space communicating with the rotatable container.

6. An apparatus according to claim 4, wherein said means for collecting the mixture of fluid and particles has a smaller diameter than the lower vessel element, to form said fourth annular space which communicates with said outlet for purified liquid flowing from said rotating container.

7. An apparatus according to claim 1 wherein said rotatable container is funnel-shaped and provided with a central, hollow shaft which is removably connected at its upper end to said drive shaft and the lower end of which discharges into a said collecting means, said hollow shaft having in its wall at least one opening for establishing a communication with said collecting means.

8. An apparatus according to claim 7, wherein the upper end of said central hollow shaft is provided with a ring-shaped flange defining the lower opening of the first annular space.

9. An apparatus according to claim 1, wherein the inner end of said upper horizontal wall of said container is arranged substantially in the same vertical plane as the outer end of said guide flange.

* * * * *